US009784987B2

(12) United States Patent
Hill et al.

(10) Patent No.: US 9,784,987 B2
(45) Date of Patent: *Oct. 10, 2017

(54) APODIZATION FOR PUPIL IMAGING SCATTEROMETRY

(71) Applicant: KLA-Tencor Corporation, Milpitas, CA (US)

(72) Inventors: Andrew V. Hill, Sunnyvale, CA (US); Amnon Manassen, Haifa (IL); Barak Bringoltz, Rishon le Tzion (IL); Ohad Bachar, Timrat (IL); Mark Ghinovker, Yoqneam Ilit (IL); Zeev Bomzon, Kiryat Tivon (IL); Daniel Kandel, Aseret (IL)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/799,132

(22) Filed: Jul. 14, 2015

(65) Prior Publication Data

US 2015/0316783 A1 Nov. 5, 2015

Related U.S. Application Data

(63) Continuation of application No. 13/936,529, filed on Jul. 8, 2013, now Pat. No. 9,091,650.

(Continued)

(51) Int. Cl.
*G01B 11/14* (2006.01)
*G02B 27/58* (2006.01)

(Continued)

(52) U.S. Cl.
CPC .............. *G02B 27/58* (2013.01); *G01B 11/00* (2013.01); *G01N 21/47* (2013.01); *G01N 21/55* (2013.01);

(Continued)

(58) Field of Classification Search
CPC ....................................................... G01B 11/14

(Continued)

(56) References Cited

U.S. PATENT DOCUMENTS

| 6,628,381 B1 * | 9/2003 | Komem | G01N 21/9501 |
| | | | 356/237.4 |
| 7,580,559 B2 * | 8/2009 | Latypov | G03F 7/70291 |
| | | | 359/290 |

(Continued)

FOREIGN PATENT DOCUMENTS

| CN | 102668052 A | 9/2012 |
| TW | 201233473 A | 8/2012 |
| TW | 201241576 A | 10/2012 |

*Primary Examiner* — Roy M Punnoose
(74) *Attorney, Agent, or Firm* — Suiter Swantz pc llo

(57) ABSTRACT

The disclosure is directed to various apodization schemes for pupil imaging scatterometry. In some embodiments, the system includes an apodizer disposed within a pupil plane of the illumination path. In some embodiments, the system further includes an illumination scanner configured to scan a surface of the sample with at least a portion of apodized illumination. In some embodiments, the system includes an apodized pupil configured to provide a quadrupole illumination function. In some embodiments, the system further includes an apodized collection field stop. The various embodiments described herein may be combined to achieve certain advantages.

26 Claims, 15 Drawing Sheets

Related U.S. Application Data

(60) Provisional application No. 61/730,383, filed on Nov. 27, 2012.

(51) Int. Cl.
    *G01N 21/55*     (2014.01)
    *G01N 21/47*     (2006.01)
    *G01B 11/00*     (2006.01)
    *G03F 7/20*     (2006.01)

(52) U.S. Cl.
    CPC ...... *G03F 7/70625* (2013.01); *G03F 7/70633* (2013.01); *G01N 2201/068* (2013.01); *G01N 2201/06113* (2013.01)

(58) Field of Classification Search
    USPC .......................................................... 356/625
    See application file for complete search history.

(56) References Cited

U.S. PATENT DOCUMENTS

| | | | |
|---|---|---|---|
| 7,589,832 B2 | 9/2009 | Den Boef et al. | |
| 7,619,735 B2* | 11/2009 | Milshtein | G01N 21/8806 356/340 |
| 8,500,725 B2* | 8/2013 | Raksi | G02B 27/0075 606/5 |
| 8,878,258 B2 | 11/2014 | Monfray et al. | |
| 9,091,650 B2* | 7/2015 | Hill | G03F 7/70625 |
| 2003/0137659 A1* | 7/2003 | Milshtein | G01N 21/8806 356/237.2 |
| 2005/0057755 A1 | 3/2005 | Johnson et al. | |
| 2005/0168790 A1* | 8/2005 | Latypov | G03F 7/70291 359/239 |
| 2005/0200850 A1 | 9/2005 | Borden et al. | |
| 2007/0046953 A1* | 3/2007 | De Groot | G01B 11/0675 356/512 |
| 2007/0081167 A1* | 4/2007 | De Groot | G01B 11/0675 356/503 |
| 2007/0195315 A1 | 8/2007 | Goldberg et al. | |
| 2008/0037134 A1 | 2/2008 | Boef et al. | |
| 2011/0069312 A1 | 3/2011 | Kandel et al. | |
| 2011/0108892 A1 | 5/2011 | Monfray et al. | |
| 2013/0114085 A1* | 5/2013 | Wang | G01N 21/55 356/445 |
| 2013/0182263 A1* | 7/2013 | Shchegrov | G01B 9/02 356/512 |
| 2014/0016125 A1* | 1/2014 | Sullivan | G01N 21/9501 356/237.5 |

* cited by examiner

APODIZATION FOR PUPIL IMAGING SCATTEROMETRY

CROSS-REFERENCE TO RELATED APPLICATION

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

Related Applications

For purposes of the USPTO extra-statutory requirements, the present application constitutes a continuation patent application of United States Non-Provisional Patent Application entitled APODIZATION FOR PUPIL IMAGING SCATTEROMETRY, naming Andrew V. Hill, Amnon Manassen, Barak Bringoltz, Ohad Bachar, Mark Ghinovker, Zeev Bomzon, and Daniel Kandel, as inventors, filed Jul. 8, 2013, application Ser. No. 13/936,529, which claims priority to United States Provisional Patent Application entitled APODIZATION FOR PUPIL IMAGING SCATTEROMETRY METROLOGY, naming Andy Hill, Amnon Manassen, Barak Bringoltz, Ohad Bachar, Mark Ghinovker, Zeev Bomzon, and Daniel Kandel, as inventors, filed Nov. 27, 2012, Application Ser. No. 61/730,383. U.S. Non-Provisional patent application Ser. No. 13/936,529; and U.S. Provisional Patent Application Ser. No. 61/730,383 are each incorporated herein by reference in their entirety.

TECHNICAL FIELD

The present disclosure generally relates to the field of optical metrology and more particularly to apodization for an optical metrology system.

BACKGROUND

Optical metrology is often utilized to measure optical and/or structural characteristics of either device or test features during semiconductor manufacture. For example, optical or structural characteristics may include critical dimensions such as height, side wall angle, pitch, linewidth, film thickness, refractive indices, and overlay between different layers or between exposures within a single layer. Apodization may be implemented in optical metrology systems to control angular and spatial distribution of illumination at well-defined locations along the optical path. Apodization is particularly important when metrology accuracy and precision depends on the ability to retrieve high fidelity spectroscopic or angular information from small metrology targets. In such cases, there is a need to prevent signal contamination resulting from either unwanted scattering from areas outside a designated metrology target on a sample or due to scattering from intermediate optical components or apertures along the optical path.

In the case of an angle resolved (pupil imaging) scatterometer, a known practice in the art is the combination of: (1) a simple flat top aperture (pupil) stop in the illumination path which restricts the illumination numerical aperture (NA) so that different diffraction orders from the metrology target can be isolated in the collection pupil; and (2) a simple flat top field stop in the illumination path to localize illumination on a small target. With the foregoing architecture, the illumination field stop becomes the limiting aperture of the pupil imaging system. The hard edges of the illumination field stop cause ringing in the images of the illumination aperture stop, and the ringing results in interaction or interference between orders (e.g. 0th order and 1st order) in the pupil image. One method of resolving this problem is field apodization in the illumination path of the optical metrology system. With field apodization, the introduction of a smoothly varying transmission function in the field results in a smoothly varying and rapidly decaying function in the conjugate pupil plane, effectively suppressing the ringing which results in interference between orders.

The foregoing approach may be appropriate for a spatially incoherent system with illumination etendue to spare. However, for optical metrology systems employing coherent illumination sources, such as a laser-based system with high spatial and temporal coherence, substantial noise issues emerge. Shaping the spatially coherent illumination beam so that it has low tails in the field plane is desirable in order to minimize periphery contamination and diffraction by the edge of the target. Low tails in the pupil plane are desirable to minimize interaction and interference between diffraction orders and clipping by the objective pupil. The beam can potentially be shaped by some combination amplitude and phase apodization in the illumination field stop or the illumination aperture stop. To average out the effects of target noise, it is desirable to scan the spatially coherent illumination spot over the target during a measurement. If beam shaping is performed at the illumination field plane, and the spot scanning mechanism is situated before this field plane, then the beam shape in the field and pupil planes will change as the spot scans across the field apodizer. This introduces fluctuations in the overall beam intensity as well as asymmetries in the distribution of light in the pupil.

SUMMARY

The present disclosure is directed to curing some or all of the foregoing deficiencies in the art utilizing one or more of the apodization schemes described below.

Various embodiments of the disclosure are directed to a system for performing optical metrology including at least one illumination source configured to illuminate the sample and at least one detector configured to receive at least a portion of illumination scattered, reflected, or radiated from the sample. At least one computing system communicatively coupled to the one or more detectors may be configured to determine at least one spatial attribute of the sample, such as an optical or structural characteristic, based upon the detected portion of illumination.

The system may include an apodizer or an apodized pupil disposed within a pupil plane of the illumination path. The apodizer may be configured to apodize illumination directed along the illumination path. In some embodiments, the system may further include an illumination scanner disposed along the illumination path and configured to scan a surface of the sample with at least a portion of the apodized illumination. The system may further include an illumination field stop configured to block a portion of illumination directed along the illumination path from scanning the surface of the sample and a collection field stop configured to block a portion of illumination directed along the collection path from being received by the detector.

In some embodiments, the system may include an apodized pupil disposed along the illumination path. The apodized pupil may include at least four elongated apertures configured to provide a quadrupole illumination function. The apodized pupil may be further configured to apodize illumination directed along the illumination path. Further, an illumination field stop disposed along the illumination path may be configured to block a portion of illumination directed along the illumination path from impinging upon or scanning the surface of the sample.

In some embodiments, the system may include an apodizer disposed within a pupil plane of the illumination path and may further include an apodized collection field stop disposed along the collection path. The apodized collection field stop may be configured to apodize illumination directed along the collection path and further configured to block a portion of illumination directed along the collection path from being received by the detector.

Those skilled in the art will appreciate that the foregoing embodiments and further embodiments described below may be combined to achieve various advantages. Accordingly, the configurations described herein should not be construed as limitations of the disclosure unless otherwise noted. Further, it is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings.

FIGS. 1A through 10B generally illustrate apodization schemes for an optical metrology system 100, such as an angle resolved (pupil imaging) scatterometer or the like. According to various embodiments, apodization at the pupil and/or detector plane enables high performance metrology on targets with relatively small dimensions. Further, the embodiments that follow include configurations associated with certain advantages in measurement quality, performance, and/or precision. It is noted that the embodiments described below serve an illustrative purpose and that various portions of multiple embodiments may be combined to arrive at further embodiments having selected advantages.

In general, the following embodiments are directed to one or more of the following advantages. The embodiments of system 100 may include configurations for shaping illumination directed along an illumination path to avoid illuminating outside of a target region of a metrology sample 102, such as a semiconductor wafer or mask. Further, the embodiments of system 100 may include configurations for mitigating or excluding illumination diffracted or scattered from optical surfaces and/or aperture edges along the illumination path to avoid contaminating pupil regions. The embodiments of system 100 may further include configurations for shaping or excluding stray illumination reflected, scattered, or radiated along a collection path to avoid detection of illumination from regions outside of the target region of the sample 102. For instance, some configurations may be directed to blocking or excluding portions of illumination diffracted from an objective lens or a collection field stop. Further goals or advantages are discussed below with respect to the following embodiments of system 100.

Figure 1A:
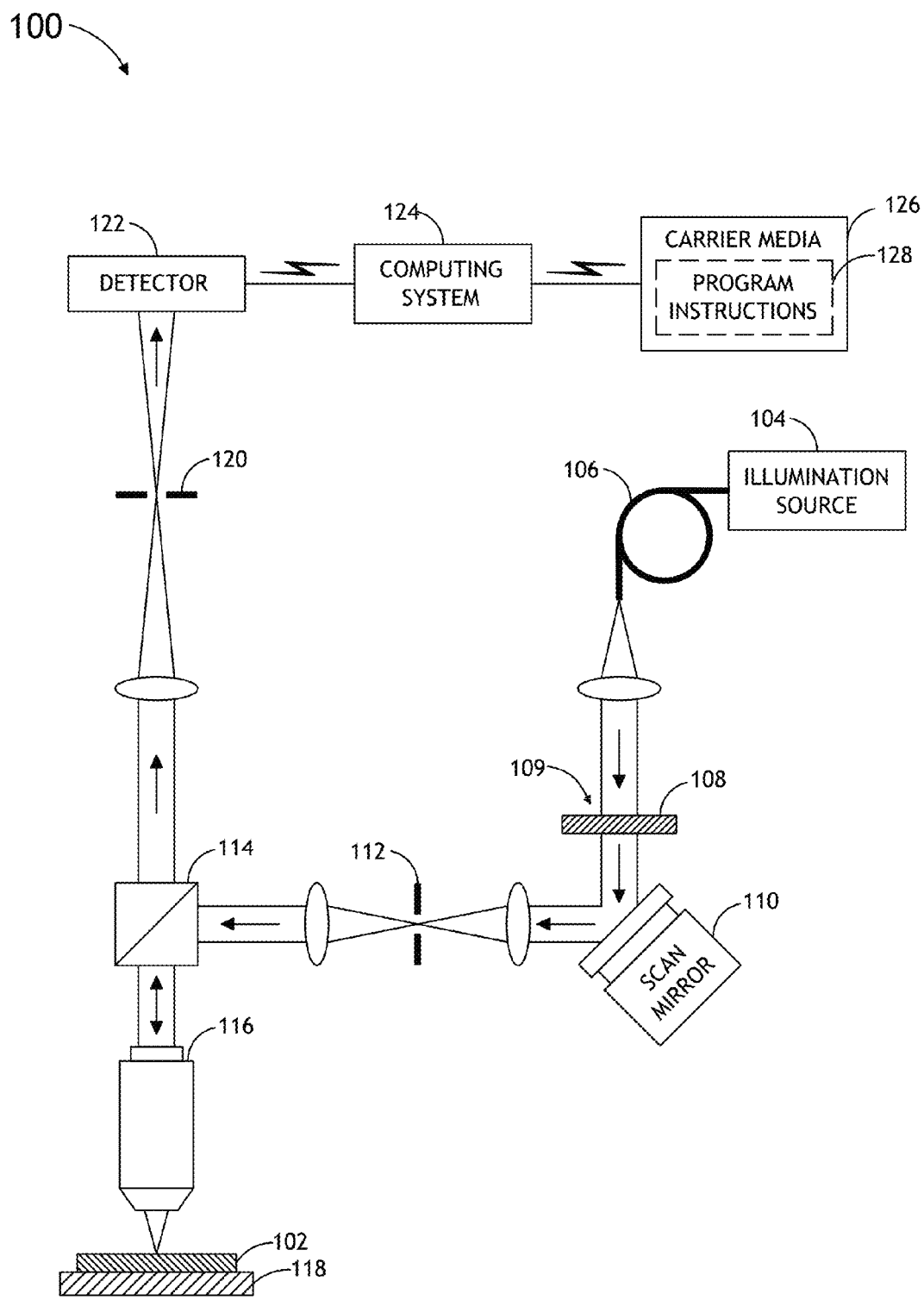
FIG. 1A is a block diagram illustrating an optical metrology system including an apodizer disposed within a pupil plane of the system, in accordance with an embodiment of this disclosure.

As shown in FIG. 1A, the system 100 may include at least one spatially coherent (e.g. laser) or incoherent (e.g. laser sustained plasma "LSP" or laser driven light source "LDLS") illumination source 104. Several of the embodiments herein are directed to an optical metrology systems based on spatially coherent illumination sources; however, many of the advantages provided by the discussed configurations are applicable to systems based on spatially incoherent illumination sources as well. In some embodiments, the illumination source 104 may be configured to provide illumination along an optical fiber 106 leading to a free space illumination path.

In some embodiments, the system 100 includes an apodizer 108, such as standalone apodization element or an apodized pupil, disposed within the pupil plane 109 of the illumination path. The system 100 may further include an illumination field stop 112 disposed along the illumination path. The illumination field stop 112 may be configured to block a portion of the illumination directed along the illumination path to localize illumination at a targeted region of the sample 102 and filter parasitic (scattered or diffracted) illumination from upstream components.

Figure 2:
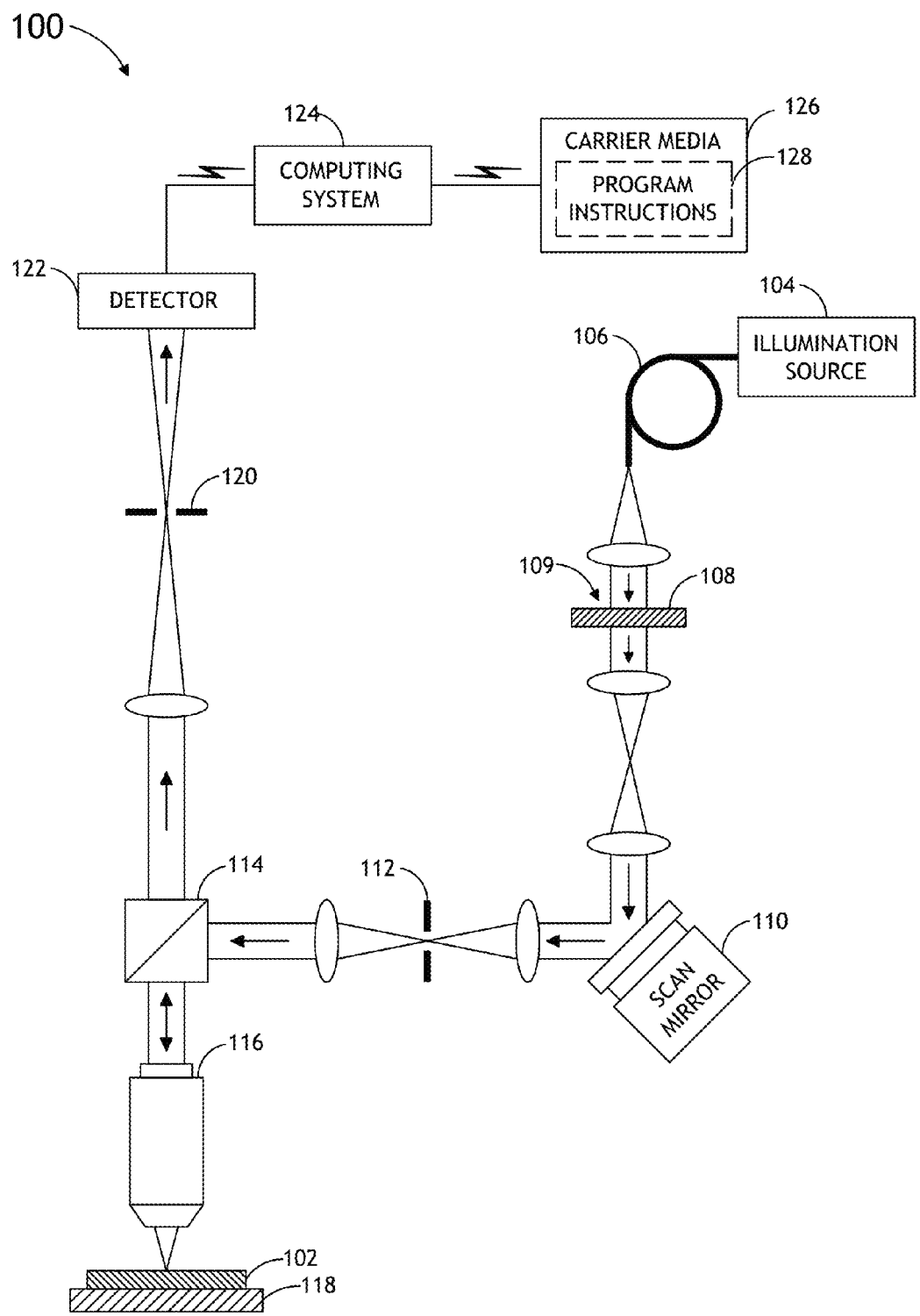
FIG. 2 is a block diagram illustrating the optical metrology system further including an illumination scanner disposed within the pupil plane of the system, in accordance with an embodiment of this disclosure.
Figure 5:
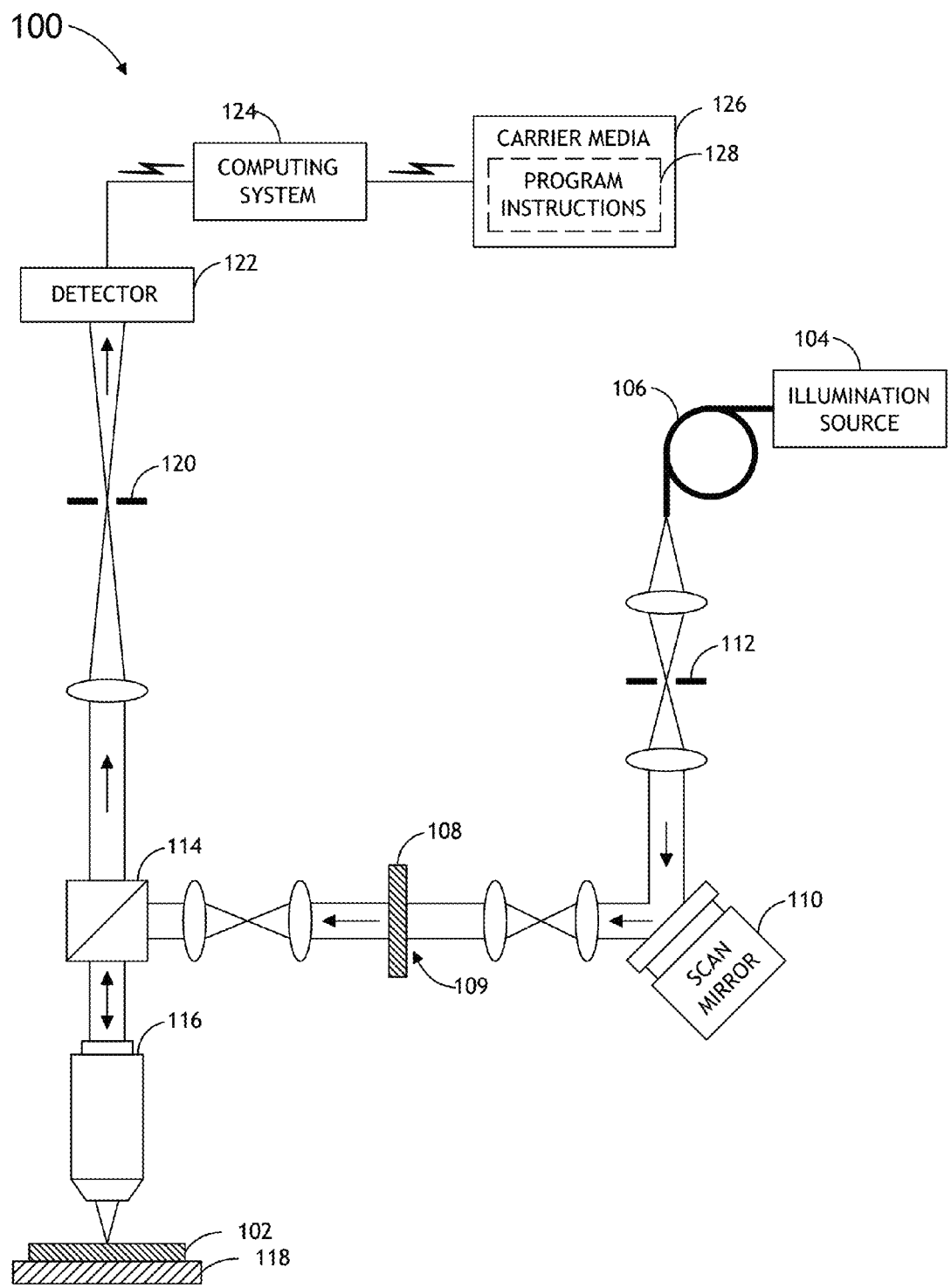
FIG. 5 is a block diagram illustrating the optical metrology system, wherein the apodizer is disposed after the illumination field stop and the illumination scanner, in accordance with an embodiment of this disclosure.

In some embodiments, the system 100 further includes an illumination scanner 110, such as a scanning mirror, disposed between the apodizer 108 and the illumination field stop 112. For example, the illumination optics may be arranged such that illumination from the illumination source 104 is directed through the apodizer 108 and then scanned across the illumination field stop 112 by the illumination scanner 110. Alternatively, as shown in FIG. 5, the illumination optics may be arranged such that illumination from the illumination source 104 is directed through the illumination field stop 112 and then scanned across the apodizer 108 by the illumination scanner 110. The illumination scanner 110 may include or may be coupled to one or more actuators enabling the illumination scanner 110 to spot scan a targeted region of sample 102 with apodized illumination that is further shaped according to the illumination field stop 112. The illumination optics may be further arranged such the illumination scanner 110 is disposed within the pupil plane 109. For example, as shown in FIG. 2, the illumination scanner 110 may be conjugate to the pupil plane 109. Placing the illumination scanner 110 at the pupil plane 109 may improve stability of an apodization function provided by the apodizer 108 during the spot scan of at least a portion of the apodized illumination at the targeted region of the sample 102.

Figure 3:
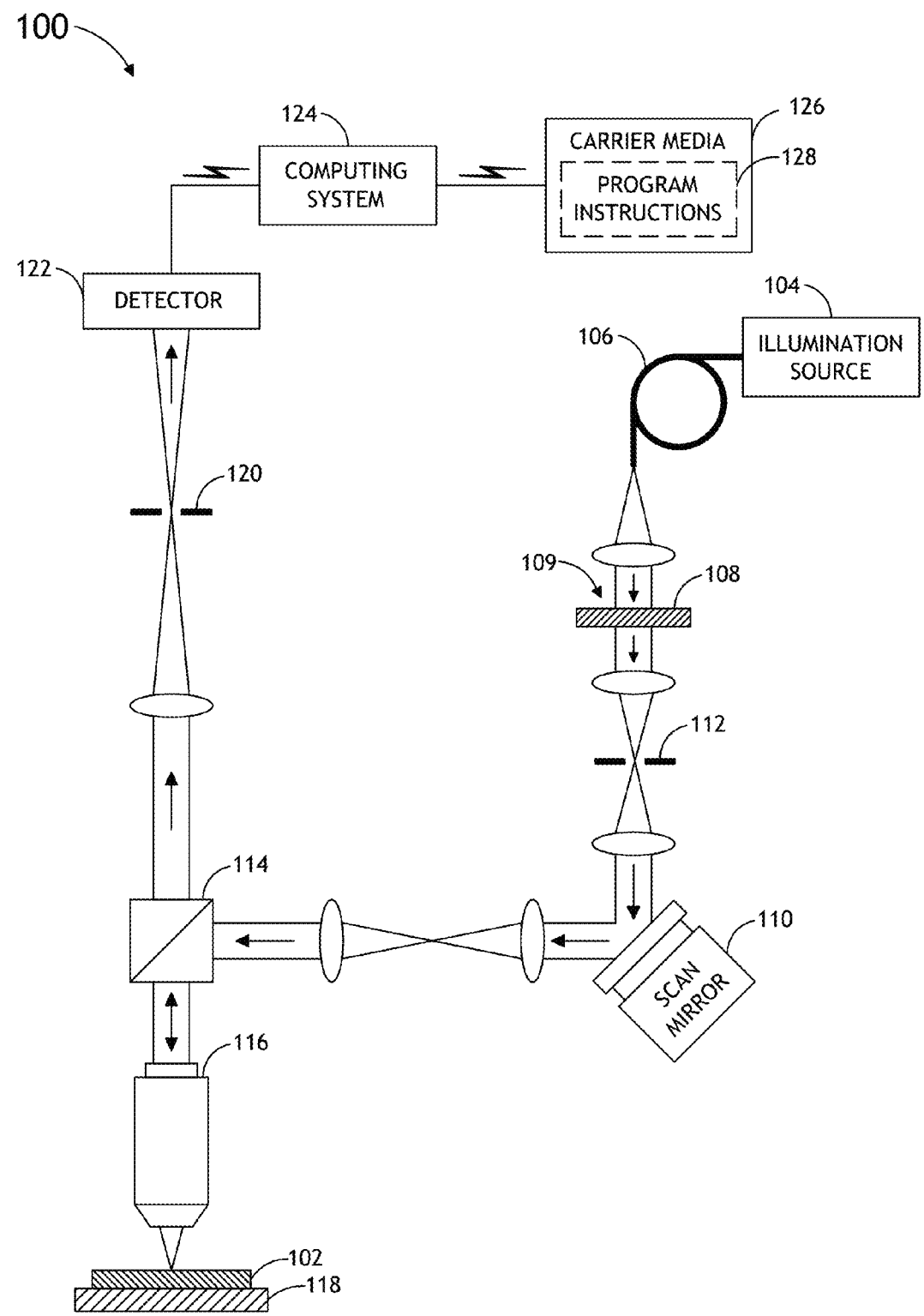
FIG. 3 is a block diagram illustrating the optical metrology system, wherein the illumination scanner is disposed after an illumination field stop, in accordance with an embodiment of this disclosure.

In some embodiments, as illustrated in FIG. 3, the apodizer 108 and the illumination field stop 112 are disposed before the illumination scanner 110. As such, illumination received by the illumination scanner 110 is apodized and further shaped according to the illumination field stop 112. This arrangement allows the illumination field stop 112 to include a smaller aperture because illumination does not need to be scanned across the field stop 112. The illumination field stop 112 can, therefore, filter off more of the spatial noise caused by the apodizer 108 and the optical fiber 106. Further, there is less chance of introducing intensity noise caused by a time dependency in diffraction of spot off edges of the illumination field stop 112. When the illumination scanner 110 is disposed after the apodizer 108 and the illumination field stop 112, strong diffractions due to scan of field stop edges may be avoided.

Figure 1B:
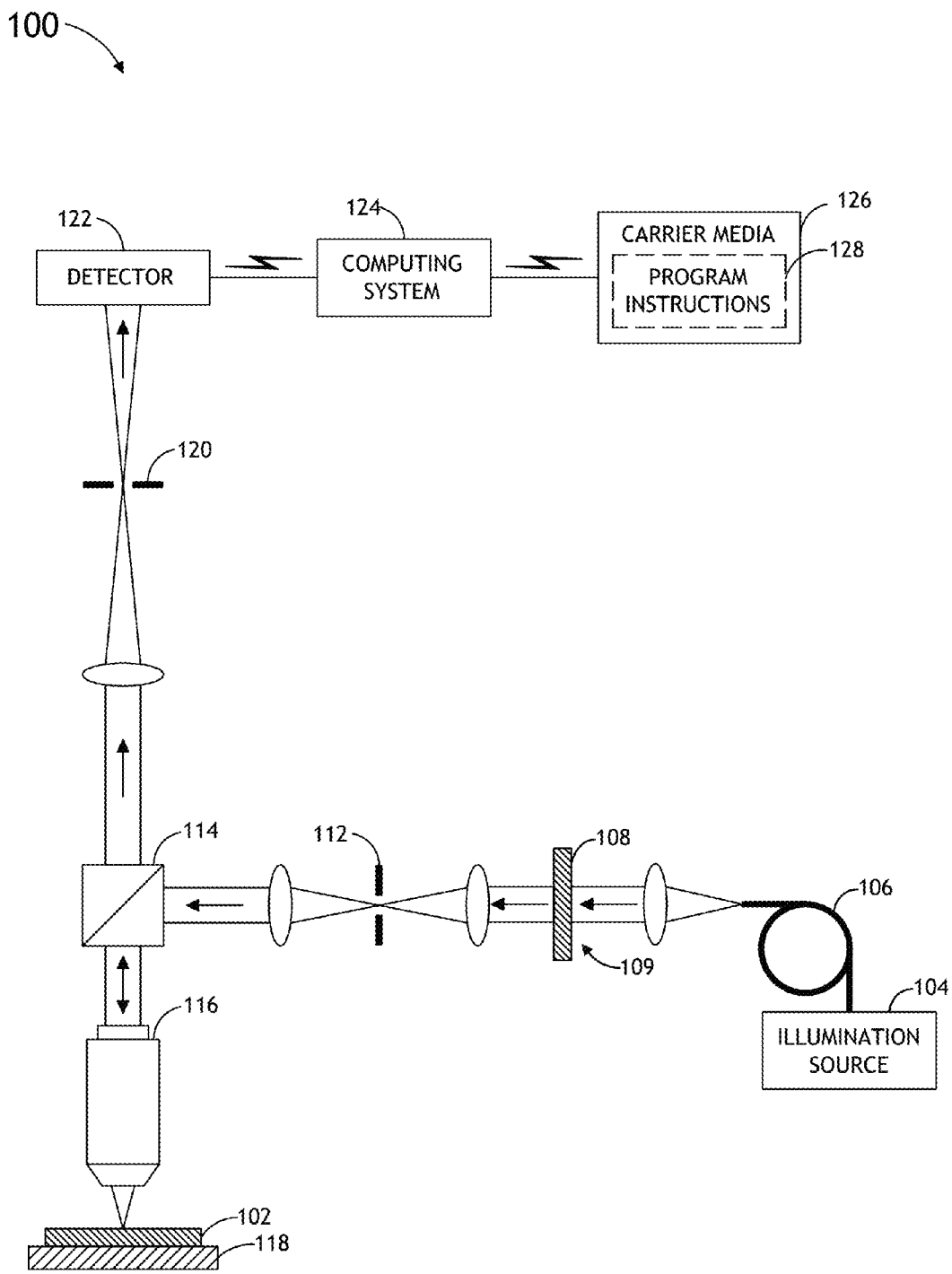
FIG. 1B is a block diagram illustrating an optical metrology system including an apodizer disposed within a pupil plane of the system, in accordance with an embodiment of this disclosure.

It is further noted that system 100 may be configured without an illumination scanner 110, as shown in FIG. 1B.

Figure 4:
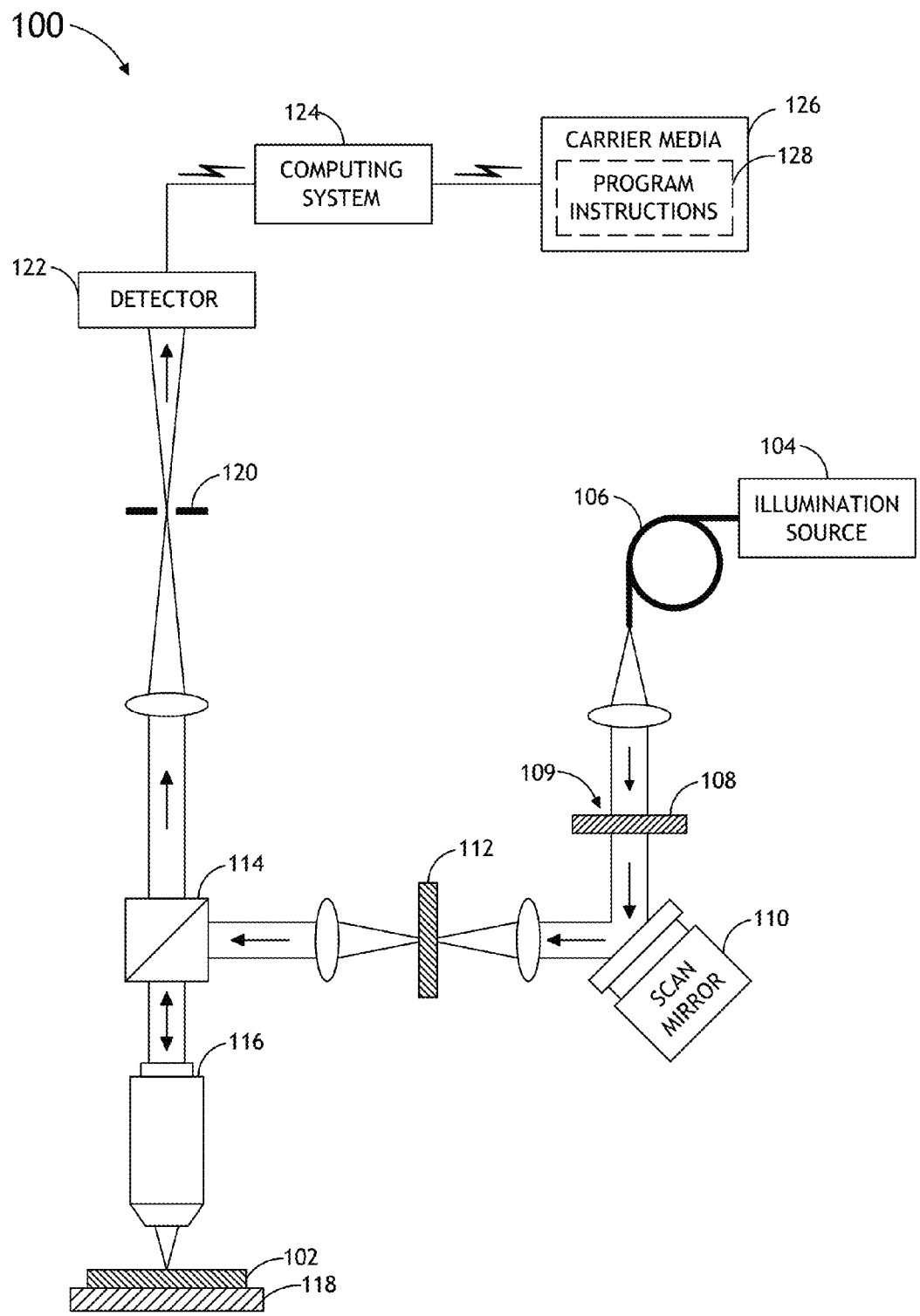
FIG. 4 is a block diagram illustrating the optical metrology system including an apodized illumination field stop, in accordance with an embodiment of this disclosure.

FIG. 4 illustrates a further embodiment where the illumination field stop 112 may also be apodized to introduce field apodization in addition to pupil apodization provided by the pupil apodizer 108. The apodized illumination field stop 112 may allow for improved ability to shape illumination directed along the illumination path. Intensity modulation and changes to pupil distribution may occur during the spot scan; however, diffraction effects due to the spot reaching edges of the illumination field stop 112 may be significantly mitigated by the apodization. Mitigation of the diffraction effects is important because, if not controlled, mixing of pupil points may occur. Since the image at the illumination field stop 112 is ultimately imaged to the sample 102, field apodization may further reduce spot intensity at the edges of the targeted region of the sample 102 and at edges of a collection field stop 120, thereby suppressing mixture of pupil points at the collection pupil.

As discussed above, FIG. 5 illustrates an embodiment where the illumination optics may be arranged such that illumination from the illumination source 104 is directed through the illumination field stop 112 and then scanned across the apodizer 108 by the illumination scanner 110. This arrangement may allow for a relatively small illumination field stop 112 disposed before the illumination scanner 110 to mitigate incoming noise from the illumination source 104 and/or optical fiber 106. Further, locating the apodizer 108 after the illumination scanner 110 may allow for enhanced ability to shape illumination scanned across the sample 102.

Figure 6:
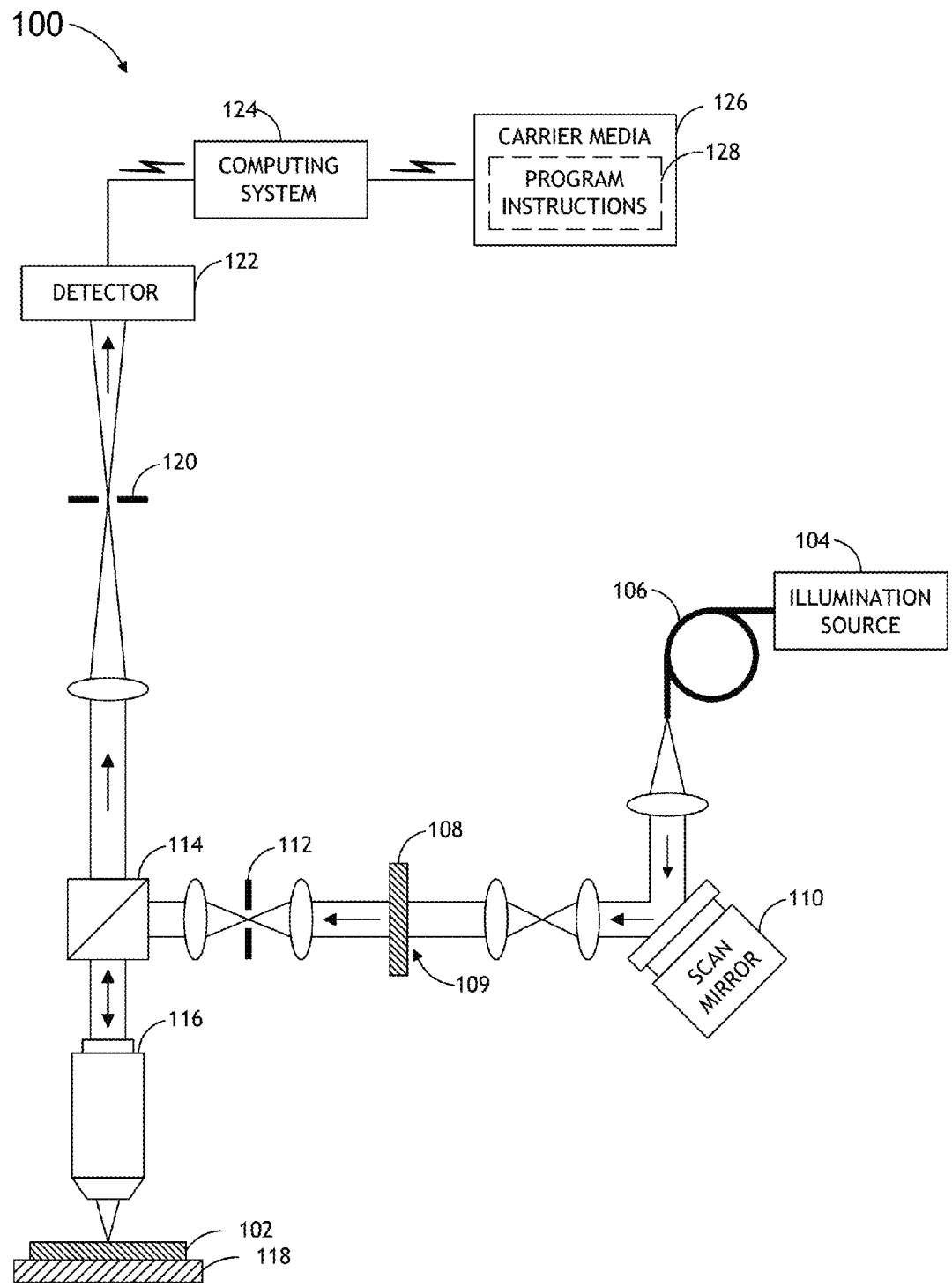
FIG. 6 is a block diagram illustrating the optical metrology system, wherein the apodizer and the illumination field stop are disposed after the illumination scanner, in accordance with an embodiment of this disclosure.

Alternatively, as shown in FIG. 6, the apodizer 108 and the illumination field stop 112 may be disposed after the illumination scanner 110. Disposing the apodizer 108 after the illumination scanner 110 may allow for a stationary apodization function in the illumination pupil because the illumination scanner 110 only affects the angle of illumination passing through the apodizer 108. Further, the illumination field stop 112 disposed after the apodizer 108 may be enabled to filter out parasitic illumination from upstream components including the apodizer 108, illumination scanner 110, optical fiber 106, and any additional illumination optics (e.g. various lenses).

The system 100 may further include a beam splitter 114 configured to direct illumination from the illumination path through an objective lens 116 to illuminate the sample 102. The system 100 may include a stage 118 configured to support the sample 102. In some embodiments, the stage 118 may further include or may be coupled to at least one actuator. The actuator may be configured to translate or rotate the stage 118 to dispose the sample 102 at a selected position. Accordingly, illumination may be targeted or scanned at a selected region of the sample 102 via actuation of the sample stage 118. Alternatively or in addition, one or more of the illumination optics, such as the objective 116 may be actuated to target a selected region of the sample 102 and/or adjust focus of illumination targeted at the sample 102.

Illumination may be scattered, reflected, or radiated by the targeted region of the sample 102. The system 100 may include at least one detector 122, such as a camera, a spectrometer, a photodiode, or any other photodetector which is configured to receive at least a portion of the scattered, reflected, or radiated illumination from the sample 102. In some embodiments, a collection field stop 120 is configured to block at least a portion of illumination directed from the sample 102 along a collection path leading to the detector 122 to filter out parasitic illumination, such as illumination diffracted or scattered by the beam splitter 114, objective lens 116 and/or any other collection optics.

Figure 7:
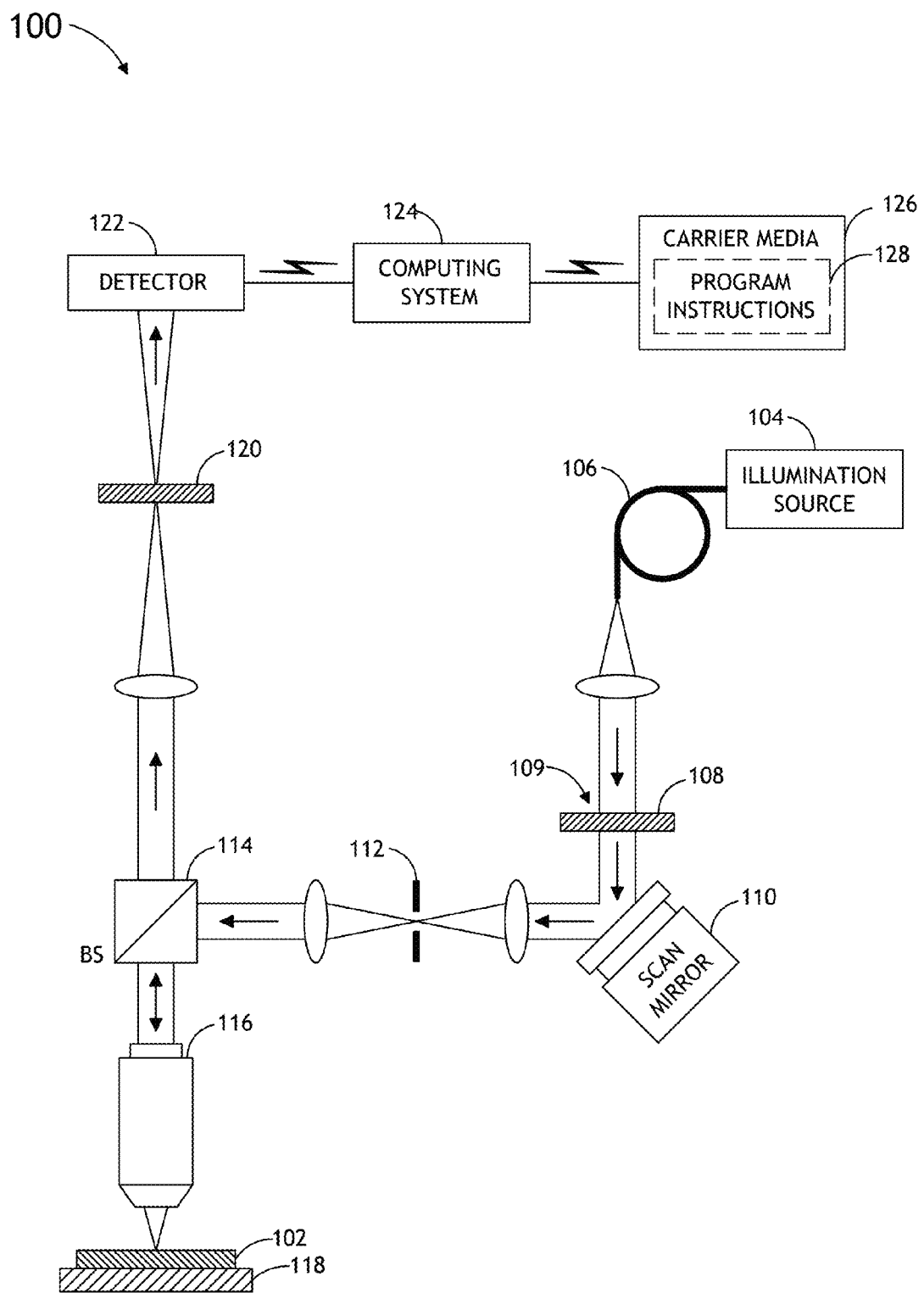
FIG. 7 is a block diagram illustrating the optical metrology system further including an apodized collection field stop, in accordance with an embodiment of this disclosure.

In some embodiments, the collection field stop 120 may further be apodized, as shown in FIG. 7. It is noted that the inclusion of the apodized collection field stop 120, among other features, may be supported by any of the embodiments described herein. The apodized collection field stop 120 may advantageously reduce sensitivity to decentering errors of beam position with respect to the center of the targeted region of the sample 102 resulting from diffraction or scattering from edges of the collection field stop 120. In particular, a collection field stop 120 with small numerical aperture (NA) may be more susceptible to decentering errors and may, therefore, benefit greatly from apodization. For further explanation, sensitivity to decentering may result from interference between wanted diffraction from a given order (e.g. $1^{st}$ order diffraction) and unwanted diffraction from another order (e.g. $0^{th}$ order diffraction) scattered from the collection field stop 120. Interference between diffraction orders can be suppressed by collection field stop apodization by shaping illumination to compensate for the diffraction or scattering effects. Further, apodization of the collection field stop 120 may reduce diffraction or scattering effects from edges of pupil apertures in pupil planes located after the collection field stop 120. Suppressing parasitic (diffracted or scattered) illumination from reaching the detector 122 may allow for improved metrology performance by reducing inaccuracy caused by decentering errors and allowing for greater precision.

The system 100 may include at least one computing system 124 communicatively coupled to the one or more detectors 122. The computing system 124 may be configured to determine at least one spatial attribute of the sample 102 based upon the detected portion of illumination scattered, reflected, or radiated from the targeted region of the sample 102. For example, the computing system 124 may be configured to determine an optical or structural characteristic of the sample 102 or defect information associated with the sample 102 according to one or more of the metrology and/or inspection algorithms known to the art. The computing system 124 may be configured to execute at least one metrology or inspection algorithm embedded in program instructions 128 stored by at least one communicatively coupled carrier medium 126. In some embodiments, the computing system 124 includes at least one single-core or multiple-core processor configured to execute the program instructions 128 from the communicatively coupled carrier medium 126. Further, it should be recognized that any of the various steps or functions described throughout the present disclosure may be carried out by a single computing system or by multiple computing systems.

Figure 8:
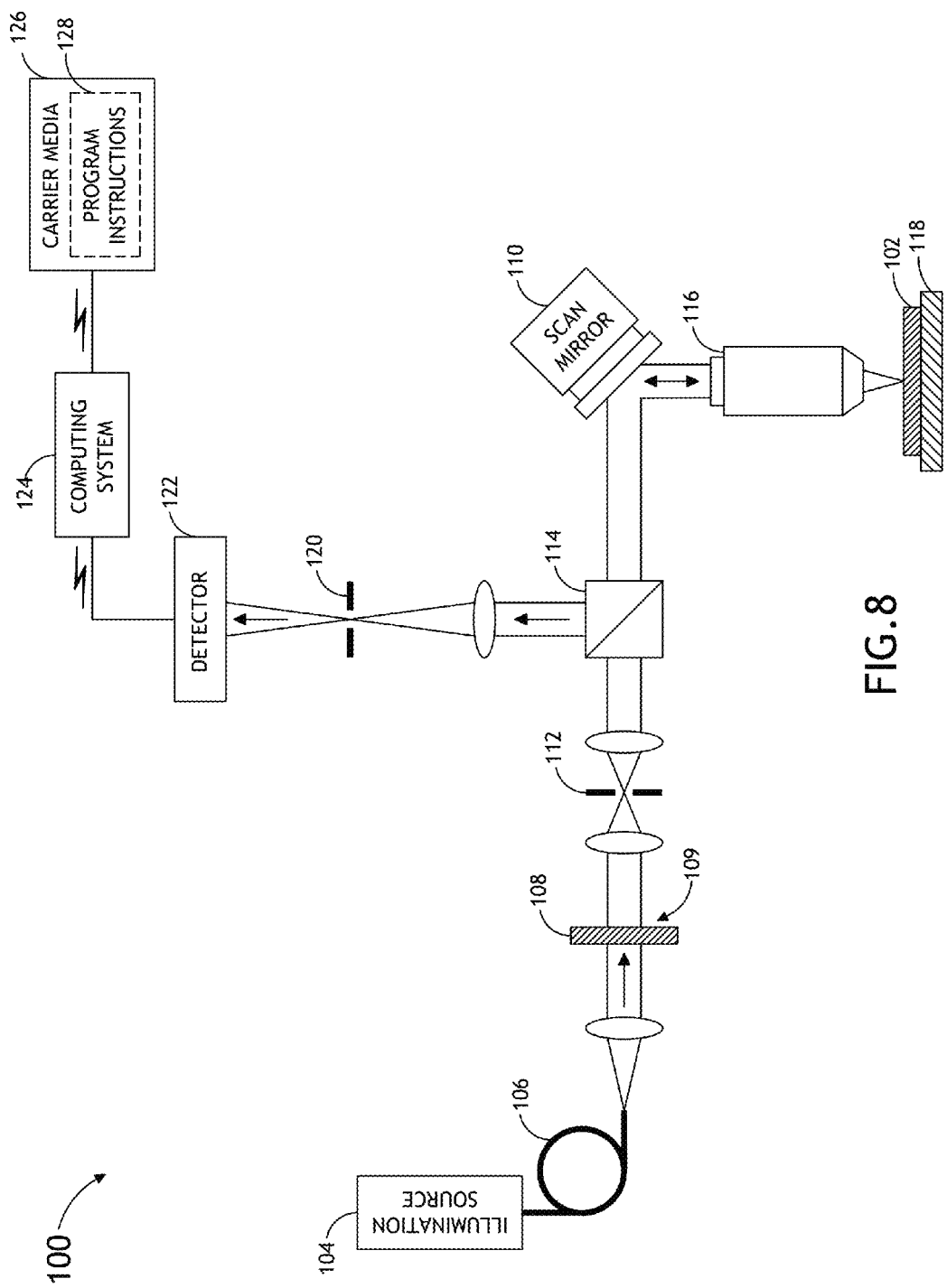
FIG. 8 is a block diagram illustrating the optical metrology system, wherein the illumination scanner is configured to scan illumination along a sample surface and further configured to descan illumination collected from the sample surface, in accordance with an embodiment of this disclosure.

FIG. 8 illustrates another embodiment of the system 100 where the illumination scanner 110 is disposed along a portion of the illumination path and a portion of the collection path. Accordingly, the illumination scanner 110 may be configured to spot scan the targeted region of the sample 102 with illumination transferred along the illumination path, and further configured to descan illumination scattered, reflected, or radiated from the sample 102 along the collection path to the detector 122. By scanning and descanning the illumination, respectively, targeted to and collected from the sample 102, the illumination scanner 110 may reduce decentering error and improve uniformity of illumination received at the detector 122. Hence, the scanning/descanning optical arrangement may improve measurement performance.

The use of apodization in pupil imaging scatterometers is described in part by US Pub. No. 20080037134, incorporated by reference herein. The apodizer 108 and, in various embodiments, the apodized illumination field stop 112 and/or the apodized collection field stop 120 may incorporate any of the apodization technologies discussed or referenced by US Pub. No. 20080037134. One of the key characteristics of an apodizer is its transmission profile as a function of radial dimension. Apodization functions are often trapezium or Gaussian in form. In some embodiments of the system 100, apodization profiles may further include, but are not limited to, top hat, optimized top hat, Gaussian, hyperbolic tangent, or Blackman forms. Rather than a polar form apodization profile, the 2D apodization distribution can also be implemented in Cartesian form by multiplying a 1D apodization distribution for the X direction by the corresponding one for the Y direction. As further discussed below, an apodization profile may be selected according to a cost functional to improve or optimize system performance.

Figure 9A:
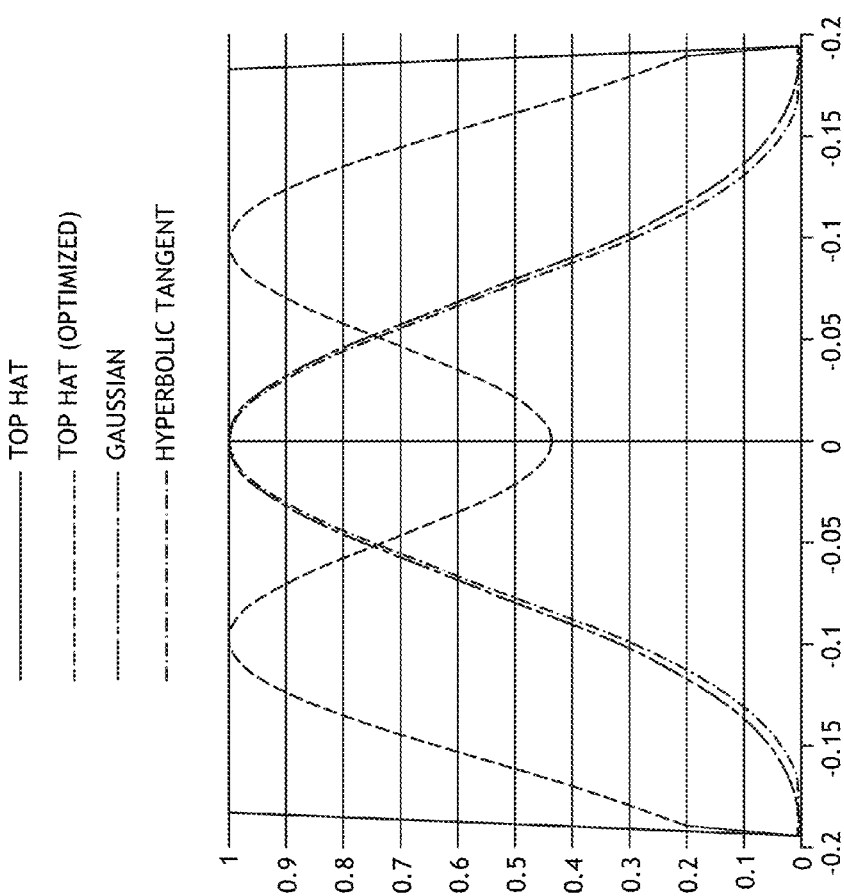
FIG. 9A is a graphical plot of exemplary apodizer scalar pupil plane profiles, in accordance with an embodiment of this disclosure.
Figure 9B:
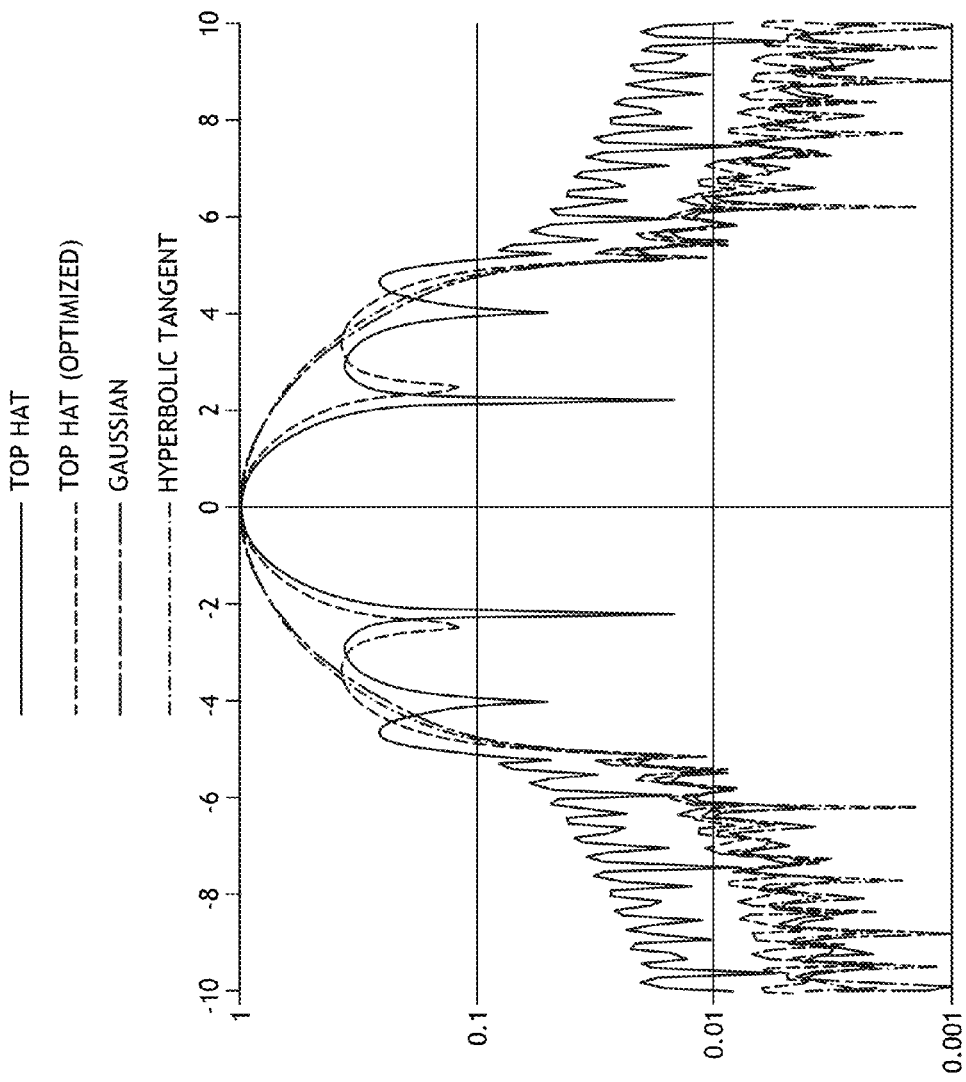
FIG. 9B is a graphical plot of wafer plane scalar intensity (logarithmic scale) for the exemplary apodizer scalar pupil plane profiles, in accordance with an embodiment of this disclosure.
Figure 9C:
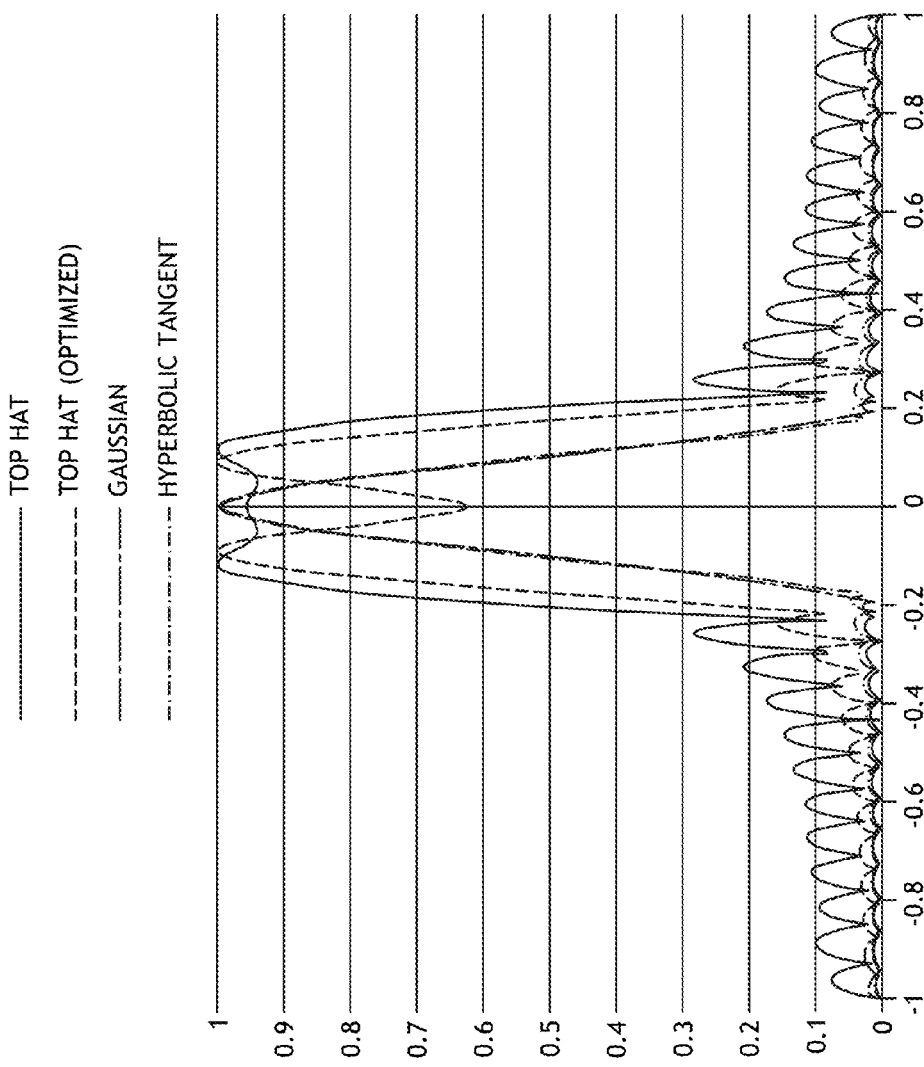
FIG. 9C is a graphical plot of resultant scalar profiles at pupil image sensor (i.e. detector) plane for the exemplary apodizer scalar pupil plane profiles, in accordance with an embodiment of this disclosure.

FIGS. 9A through 9C illustrate examples of the scalar distribution for a number of different apodization profiles and the corresponding resultant profiles at the sample imaging plane and the collection pupil plane. For example, FIG. 9A shows scalar pupil plane profiles (transmission vs. pupil coordinates) exemplary of top hat, optimized top hat, Gaussian, and hyperbolic tangent profiles. FIG. 9B shows scalar intensity at the sample imaging plane corresponding to the exemplary apodization profiles, and FIG. 9C shows the corresponding resultant scalar profiles at the detector (i.e. collection) pupil plane. As illustrated by the exemplary plots in FIGS. 9A through 9C, there may be a significant reduction of intensity in the periphery of the illumination spot at sample coordinates, thus leading to reduced signal contamination at the detector 122 from regions outside the targeted region of the sample 102.

In some embodiments, the apodization profile may be selected according to a cost functional. For example, the apodization profile may be specified for substantially maximizing tail to peak ratio at a given location in the aperture on the pupil detector 122 while substantially minimizing the overall signal and subsequent precision impact. In a 1D case, the pupil apodization profile may be selected according to the following cost functional:

$$F(p(k)) = \int_{x > x_0} dx [|\int_{-NA}^{+NA} dk p(k) e^{-ikx}|^2] + \lambda_1 \int_{k > k_0} dk |p(k) - p(0)|^2,$$

where p(k) is a pupil apodizer profile, $x_0$ defines a target range of the sample, $k_0$ defines a target range of the pupil plane, $\lambda_1$ defines relative weight for tail reduction in field plane and pupil function uniformity, and NA defines pupil aperture (in natural units). Further, in embodiments, the collection apodization profile may be selected according to the following cost functional:

$$F(p(x)) = \int_{k > k_0} dk [|\int_{-L/2}^{+L/2} dx p(x) e^{+ikx}|^2] + \lambda_2 \int_{x > x_1} dx [|p(x) - p(0)|],$$

where p(x) is a field apodizer profile, $x_1$ defines a target range of the sample, $k_0$ defines a target range of the pupil plane, $\lambda_2$ defines relative weight for tail reduction in field plane and collection field stop function uniformity, and L defines collection field stop size.

Figure 9D:
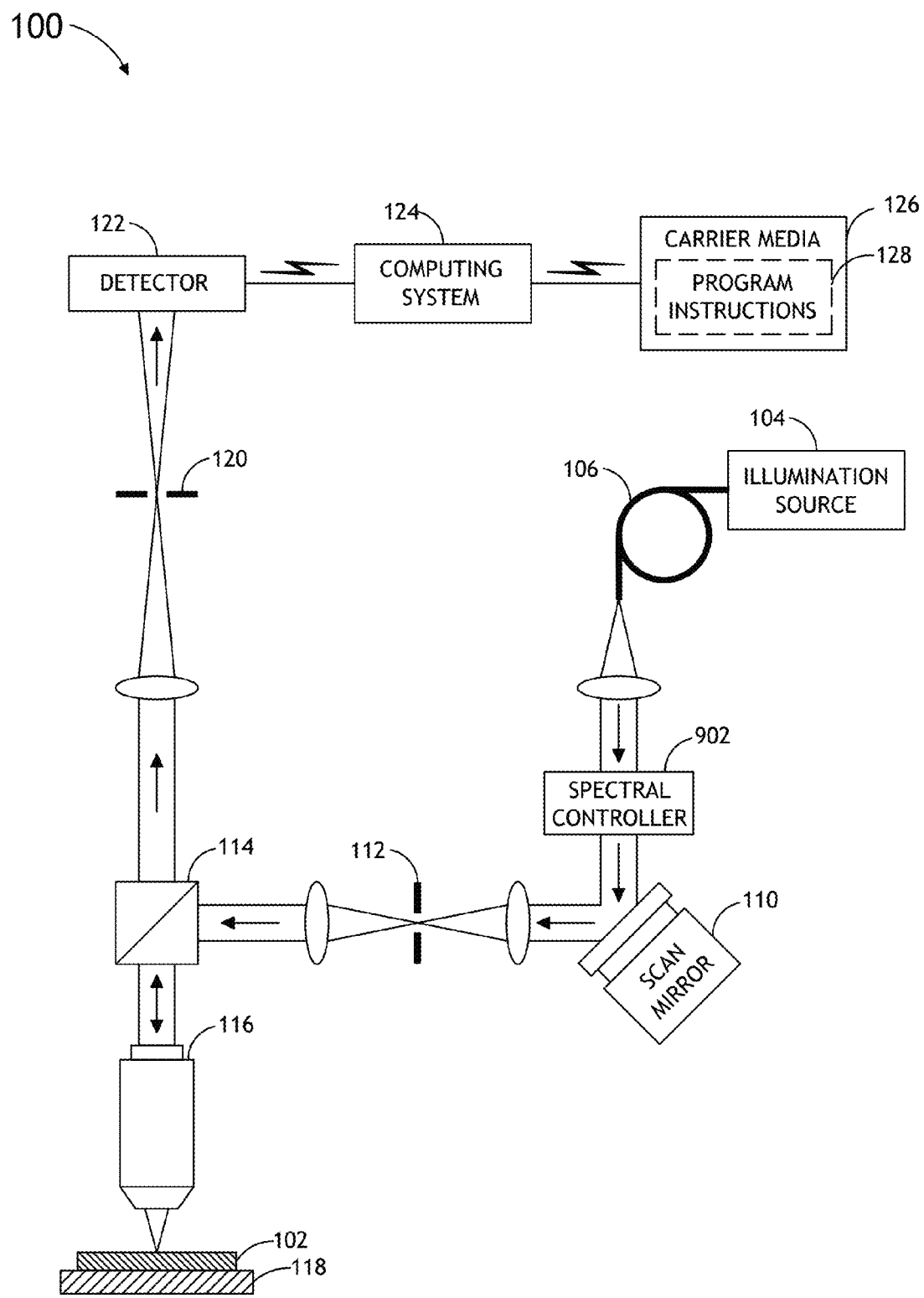
FIG. 9D is a block diagram illustrating an optical metrology system equipped with a spectral controller, in accordance with an embodiment of this disclosure.

In some embodiments, the illumination spectrum can be varied as part of the metrology recipe setup. For example, the illumination spectrum may be controlled utilizing a spectral controller or spatial light modulator (SLM), such as a DLP mico-mirror array manufactured by TEXAS INSTRUMENTS. For example, an apodization profile may be determined and controlled utilizing target related parameters such as size, pitch, or reflectivity as a function of wavelength together with similar characteristics of target proximity according to a cost functional similar to the apodization profile selection cost functions described above. As shown in FIG. 9D, a spectral controller 902 may be disposed illumination path. The spectral controller may be configured to affect apodization by controlling a spectrum of illumination directed along the illumination path. In some embodiments, the spectral controller includes a micro-mirror array, a plurality of active shutters, or a selected filter.

Figure 10A:
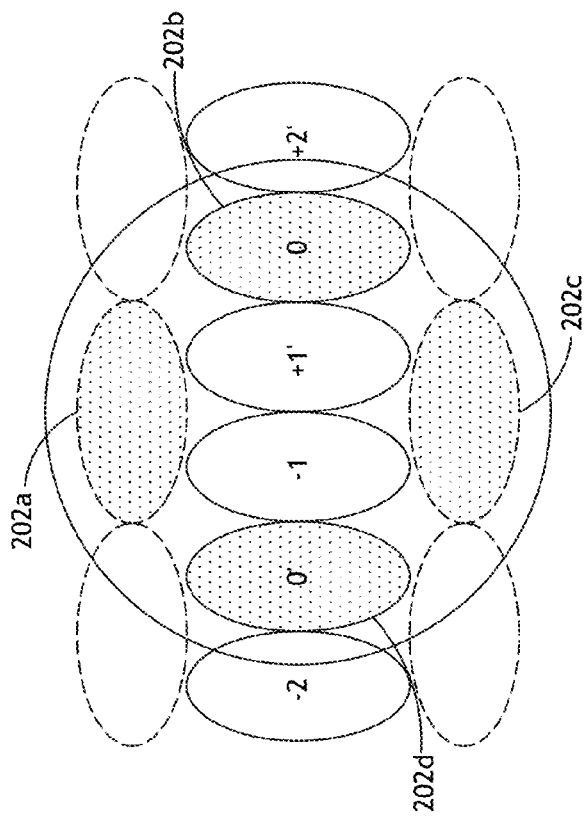
FIG. 10A illustrates a pupil configured for a quadrupole illumination function, in accordance with an embodiment of this disclosure.
Figure 10B:
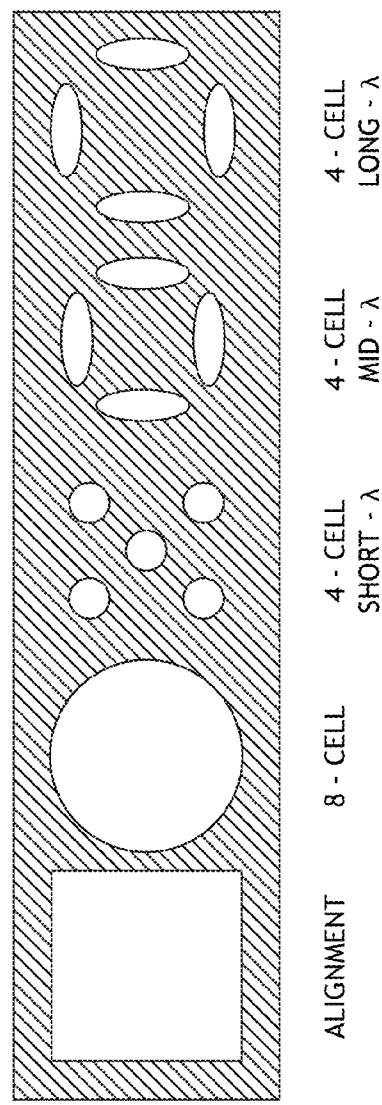
FIG. 10B illustrates a plurality of pupil configurations, in accordance with an embodiment of this disclosure.

Despite advantages of strong apodization functions, there may be an associated loss of signal and subsequent loss of metrology precision. In some embodiments, the shape of the pupil, hence the pupil function, may be modified to regain metrology precision. FIGS. 10A and 10B illustrate various pupil functions 200 that may be applied to the apodized pupil 108. In some embodiments, as illustrated in FIG. 10A, the spots (pupil apertures) 202a-202d may be elongated in a direction orthogonal to diffraction in order to increase the size of the diffraction spot. Further, the apodized pupil 200 may be configured for quadrupole illumination, including at least four elongated apertures 202a-202d, to ensure that the elongation is always in a direction orthogonal to the diffraction and to allow for capturing orders from higher ratios of illumination wavelength to grating pitch. Further embodiments of the pupil 200 are illustrated in FIG. 10B. However, it is contemplated that various modifications may be incorporated without departing from the scope of this disclosure.

While some of the embodiments discussed above are directed to apodization functions that are intensity modulated only, it is emphasized here that the apodization functions may be complex functions combining intensity modulation together with phase apodization. For instance, the cost functions p(x) and p(k) given above for field and pupil apodization may be rewritten as $p=|p|e^{i\psi}$, where |p| reflects intensity modulation of the apodizer and $\psi$ phase modulations.

Apodization elements may be manufactured to several technologies known to the art. Some examples include half-tone amplitude transmission masks, varying neutral density masks, and phase modulated masks. Lithographic techniques are known to work particularly well for half-tone amplitude masks and for phase masks with discrete phase steps (e.g. approximately 8 levels). In some embodiments, the apodization elements may be made using standard e-beam writing techniques in resist on photomask blanks to produce the high precision apodization required for the optical metrology system 100.

Although the embodiments discussed above and illustrated by the figures show a single optical column (i.e. single-line illumination path and single-line collection path), it will be appreciated by those skilled in the art that multiple paths may exist in an optical column. For example, multi-path optical arrangements may be employed for different illumination and collection polarization states, as described in US Pub. No. 2011000108892, incorporated by reference herein. In some embodiments, two or more polarization paths may be simultaneously apodized by a common apodizer or there may be separate apodizers for each polarization path.

The combination of a scanning beam with apodization may provide significant advantages. Scanning a spatially coherent beam allows the illumination spot size to be controlled for each target without the loss of light that changing the field stop size imposes. A system that supports spatially coherent illumination enables the smallest possible spot on the target and subsequently the smallest possible target sizes. Furthermore, apodizing the pupil function (as opposed to the field) allows critical distribution to be kept stationary in the illumination pupil during the spot scan. It is further noted that a scanning module may be utilized to induce intensity modulations in the illumination beamed from a source. Accordingly, the spot incident on a sample may have a wafer coordinate dependent overall intensity. This may allow for an effectively apodized illumination field stop for an incoherent light source. An important advantage of this combination is the improved flexibility in selection of the apodization function. Further, an illumination field apodizer is introduced that does not inflict scattering side-effects due to its fabrication process.

Additional advantages of the foregoing embodiments include, but are not limited to: reduction or elimination of signal contamination on the collection pupil from scattered light from outside the targeted region; reduction or elimination of signal contamination on the collection pupil from scattered light from apertures along the illumination or collection optical paths; stable illumination pupil distribution during a spot scan; reduced interaction between the spot and field stops and target edge during a scan; and controlled scanning allowing tradeoff between periphery interaction or target edge diffraction and better target noise averaging.

Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. Program instructions implementing methods such as those described herein may be transmitted over or stored on carrier media. A carrier medium may include a transmission medium such as a wire, cable, or wireless transmission link. The carrier medium may also include a storage medium such as a read-only memory, a random access memory, a magnetic or optical disk, or a magnetic tape.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

What is claimed is:

1. An optical metrology apparatus, comprising:
   at least one illumination source configured to provide illumination along an illumination path;
   an apodizer disposed within a pupil plane of the illumination path, the apodizer configured to apply an apodization profile to the illumination directed along the illumination path, wherein the apodization profile imparts at least one of intensity modulation or phase modulation on the illumination directed along the illumination path;
   an illumination scanner disposed along the illumination path, the illumination scanner configured to scan a surface of a sample with at least a portion of the illumination from the apodizer; and at least one detector configured to detect a portion of illumination scattered, reflected, or radiated from the surface of the sample along a collection path.

2. The apparatus of claim 1, wherein the illumination scanner is disposed within a pupil plane of the illumination path.

3. The apparatus of claim 1, further comprising:
an illumination field stop disposed along the illumination path, the illumination field stop configured to block a portion of illumination directed along the illumination path.

4. The apparatus of claim 3, wherein the illumination scanner is disposed along the illumination path between the apodizer and the illumination field stop.

5. The apparatus of claim 3, wherein the apodizer is disposed between the at least one illumination source and the illumination scanner.

6. The apparatus of claim 3, wherein the illumination field stop is disposed between the at least one illumination source and the illumination scanner.

7. The apparatus of claim 3, wherein the illumination field stop is disposed along the illumination path between the apodizer and the illumination scanner.

8. The apparatus of claim 3, wherein the apodizer is disposed along the illumination path between the illumination scanner and the illumination field stop.

9. The apparatus of claim 3, wherein the illumination field stop comprises an apodized field stop.

10. The apparatus of claim 1, wherein the illumination scanner is further configured to direct illumination scattered, reflected, or radiated from the surface of the sample along the collection path to the at least one detector.

11. The apparatus of claim 1, wherein the at least one illumination source comprises a coherent illumination source.

12. The apparatus of claim 1, further comprising:
a collection field stop disposed along the collection path, the collection field stop configured to block a portion of illumination directed along the collection path from being detected by the detector.

13. The apparatus of claim 12, wherein the collection field stop comprises an apodized field stop configured to apodize illumination directed along the collection path.

14. The apparatus of claim 1, further comprising:
a spectral controller disposed along the illumination path, the spectral controller configured to affect apodization by controlling a spectrum of illumination directed along the illumination path.

15. The apparatus of claim 14, wherein the spectral controller includes at least one of a micro-mirror array, a plurality of active shutters, or a selected filter.

16. An optical metrology apparatus comprising:
at least one illumination source configured to provide illumination along an illumination path to illuminate a surface of a sample;
an apodized pupil disposed along the illumination path, the apodized pupil including one or more apertures;
an illumination scanner, the illumination scanner configured to scan the surface of the sample with at least a portion of the apodized illumination; and
at least one detector configured to detect a portion of illumination from the surface of the sample.

17. The apparatus of claim 16, wherein the illumination scanner is further configured to direct illumination scattered, reflected, or radiated from the surface of the sample along the collection path to the at least one detector.

18. The apparatus of claim 16, further comprising:
an illumination field stop disposed along the illumination path, the illumination field stop configured to block a portion of illumination directed along the illumination path.

19. The apparatus of claim 18, wherein the illumination field stop comprises an apodized field stop.

20. The apparatus of claim 16, wherein the at least one illumination source comprises a coherent illumination source.

21. The apparatus of claim 16, further comprising:
an apodized collection field stop disposed along the collection path, the apodized collection field stop configured to apodize illumination directed along the collection path, and further configured to block a portion of illumination directed along the collection path from being detected.

22. An optical metrology apparatus comprising:
at least one illumination source configured to provide illumination along an illumination path to illuminate a surface of a sample;
an apodizer disposed within a pupil plane of the illumination path, the apodizer configured to apodize illumination directed along the illumination path;
an illumination scanner disposed along the illumination path, the illumination scanner configured to scan a surface of the sample with at least a portion of the illumination from the apodizer; and
at least one detector configured to detect a portion of illumination scattered, reflected, or radiated from the surface of the sample along a collection path.

23. The apparatus of claim 22, further comprising:
an illumination field stop disposed along the illumination path, the illumination field stop configured to block a portion of illumination directed along the illumination path.

24. The apparatus of claim 23, wherein the illumination field stop comprises an apodized field stop.

25. The apparatus of claim 22, further comprising:
an apodized collection field stop disposed along the collection path, the apodized collection field stop configured to apodize illumination directed along the collection path, and further configured to block a portion of illumination directed along the collection path from being detected.

26. The apparatus of claim 22, wherein the at least one illumination source comprises a coherent illumination source.

* * * * *